(12) United States Patent
Okumura

(10) Patent No.: US 7,851,743 B2
(45) Date of Patent: Dec. 14, 2010

(54) ION MOBILITY SPECTROMETER

(75) Inventor: Akihiko Okumura, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 203 days.

(21) Appl. No.: 12/314,580

(22) Filed: Dec. 12, 2008

(65) Prior Publication Data

US 2009/0184241 A1   Jul. 23, 2009

(30) Foreign Application Priority Data

Dec. 14, 2007  (JP) .............................. 2007-323171

(51) Int. Cl.
*H01J 49/40* (2006.01)
*H01J 49/00* (2006.01)

(52) U.S. Cl. .................... 250/282; 250/281; 250/288; 250/299

(58) Field of Classification Search ............. 250/281, 250/282, 286, 288, 290, 292, 299
See application file for complete search history.

(56) References Cited

U.S. PATENT DOCUMENTS

| | | | | |
|---|---|---|---|---|
| 4,271,357 A | * | 6/1981 | Bradshaw et al. | 250/287 |
| 4,317,995 A | * | 3/1982 | Bradshaw et al. | 250/288 |
| 5,218,203 A | * | 6/1993 | Eisele et al. | 250/288 |
| 6,630,662 B1 | | 10/2003 | Loboda | |
| 7,112,785 B2 | * | 9/2006 | Laramee et al. | 250/288 |
| 7,265,345 B2 | | 9/2007 | Hashimoto et al. | |
| 2002/0113207 A1 | * | 8/2002 | Lee et al. | 250/288 |
| 2003/0213903 A1 | | 11/2003 | Ichimura et al. | |
| 2005/0178957 A1 | * | 8/2005 | Pusterla et al. | 250/282 |
| 2008/0073503 A1 | * | 3/2008 | Wu | 250/283 |

FOREIGN PATENT DOCUMENTS

| | | |
|---|---|---|
| JP | 2003-329646 | 5/2002 |
| JP | 2005-524196 | 4/2003 |
| JP | 2006-107929 | 10/2004 |

OTHER PUBLICATIONS

Stormy L. Koeniger et al., "An IMS-IMS Analogue of MS-MS", Anal. Chem., No. 78, No. 12, Jun. 15, 2006, pp. 4161-4174.

* cited by examiner

*Primary Examiner*—Bernard E Souw
(74) *Attorney, Agent, or Firm*—Stites & Harbison, PLLC; Juan Carlos A. Marquez, Esq.

(57) ABSTRACT

The present invention achieves an ion mobility spectrometer which is small-sized but has higher selectivity. In an interior of a drift tube, air flow moving from a detector side to an ion source side is generated, and there are arranged, in order from an upstream side of the air flow to a downstream side thereof, a first region where a flow rate increases in a flow direction, a second region where the flow rate is constant, and a third region where the flow rate decreases. Light irradiation mechanisms for dissociating an ion are provided in the second region.

8 Claims, 6 Drawing Sheets

ION MOBILITY SPECTROMETER

CLAIM OF PRIORITY

The present application claims priority from Japanese patent application JP 2007-323171 filed on Dec. 14, 2007, the content of which is hereby incorporated by reference into this application

BACKGROUND OF THE INVENTION

1. Field of the Invention

The present invention relates to an ion mobility spectrometer.

2. Description of the Related Art

There is a demand for a small-sized and portable monitoring device for speedily and accurately detecting harmful matters such as explosives, poison gas, environmental pollutants. The monitoring device based on mass spectrometry is excellent in sensitivity and selectivity and is capable of performing accurate measurement with little false detection. However, the mass spectrometer needs high vacuum, and therefore, is large in size. On the other hand, the ion mobility spectrometer is capable of detecting ions by spatially separating ions under atmospheric pressure based on the difference in the ion mobility. The ion mobility spectrometer has a feature in which a vacuum system is not needed and therefore the device is easily miniaturized. However, the ion mobility spectrometry is inferior to the mass spectrometry in selectivity and has a problem in that false detection often occurs.

Japanese Patent Publication No. 2006-107929 discloses a tandem ion mobility spectrometer. The similar device is disclosed also in Stormy L. Koeniger, Samuel I. Merenbloom, Stephen J. Valentine, Martin F. Jarrold, Harold R. Udseth, Richard D. Smith, and David E. Clemmer, Anal. Chem. 2006; 78:4161. In these tandem ion mobility spectrometers, first and second separation sections (so-called drift tubes) for spatially separating ions based on the difference in the ion mobility are arranged in series, and an ion dissociation section for dissociating ions is provided at an intermediate section therebetween. Among the ions spatially separated by the first drift tube, ions having predetermined ion mobility are introduced to the ion dissociation section and dissociated by some means in the ion dissociation section. Fragment ions generated by the ion dissociation section are spatially separated according to difference in ion mobility while passing through the second drift tube, and reach a detector at different times. Even when two kinds of substances having approximately the same ion mobility exist, these tandem ion mobility spectrometers are capable of distinguishing these kinds of substances as long as their fragment ions are different in ion mobility to such an extent they can be separated.

Japanese Patent Translation Publication No. 2005-524196 and Japanese Patent Publication No. 2003-329646 disclose a technique in which various types of ions are spatially separated and captured according to the difference in ion mobility in an interior of the drift tube of the ion mobility spectrometer. The principle used is based on the following point. Namely, when gas flow, which opposes in an ion traveling direction and has linear velocity gradually decreasing, is generated in the interior of the drift tube, movement of ion stops at a position where ion mobility and resistance force due to gas flow are balanced with each other. After ions are captured and accumulated by this technique, drift voltage is increased and the ions are discharged from the drift tube to perform detection. Using such technique can improve sensitivity and resolution of the ion mobility spectrometer, resulting in improved selectivity.

SUMMARY OF THE INVENTION

The ion mobility spectrometer is a small-sized and portable analyzer, which is used for monitoring harmful substances such as explosives, poison gas, environmental pollutants, and the like. However, there is a demand to improve selectivity to achieve accurate measurement with little false measurement.

The tandem ion mobility spectrometers disclosed in Japanese Patent Publication No. 2006-107929 and Anal. Chem. 2006;78:4161 makes it possible to distinguish ions of substances to be detected based on both the ion mobility thereof and the ion mobility of fragment ions, and therefore selectivity is remarkably improved. However, such tandem ion mobility spectrometer is composed of two drift tubes and the ion dissociation section arranged in series, and thus is large in size. For this reason, the feature of the ion mobility spectrometer is lost. According to the methods disclosed in Japanese Patent Translation Publication No. 2005-524196 and Japanese Patent Publication No. 2003-329646, sensitivity and resolution of the ion mobility spectrometer are improved, resulting in improved selectivity. However, improvement in resolution and selectivity obtained from these methods is limited.

An object of the present invention is to miniaturize a tandem ion mobility spectrometer in order to provide an ion mobility spectrometer which is small-sized and portable but has remarkably high selectivity as compared with the conventional system.

In order to attain the above object, the present invention achieves a tandem ion mobility spectrometer in which an ion separation section for separating ions generated by an ion source, an ion dissociation section, and an ion separation section for separating fragment ions generated by the ion dissociation section are integrated. The specific configuration will be described as follows. In an interior of a drift tube, air flow moving from a detector side to an ion source side is generated. In the interior of the drift tube, there are arranged, in order from an upstream side of the gas flow to a downstream side thereof, a first region where a flow rate increases in a flow direction, a second region where the flow rate is constant, and a third region where the flow rate decreases. An energy supplying mechanism for dissociating ions is provided in the second region. Ions generated by the ion source move to the detector side in the interior of the drift tube, and an ion having predetermined ion mobility, depending on the size of electric field and the flow rate of gas flow is captured and accumulated in the second region. An ion having ion mobility higher than the predetermined ion mobility passes through the third region speedily, collides with the detector, and disappears. An ion having ion mobility lower than the predetermined ion mobility stays in the first region or is pushed by the gas flow and discharged to outside of the system. When electric field intensity is increased after the ion captured in the second region is dissociated and fragment ions are generated, the generated fragment ions pass through the third region and reach the detector to be detected in decreasing order of ion mobility.

According to the tandem ion mobility spectrometer of the present invention, it is possible to achieve isolation and dissociation of ions having predetermined ion mobility and separation of fragment ions, based on the ion mobility, which are generated by dissociation in the interior of one drift tube. This achieves remarkable miniaturization as compared with the conventional tandem ion mobility spectrometer. As a result, there is provided a harmful substances monitoring device, which is small-sized and portable but has higher selectivity and less erroneous detection as compared with the conventional ion mobility spectrometer.

DESCRIPTION OF THE PREFERRED EMBODIMENTS

The following will describe an embodiment of the present invention with reference to the accompanying drawings.

Figure 1:
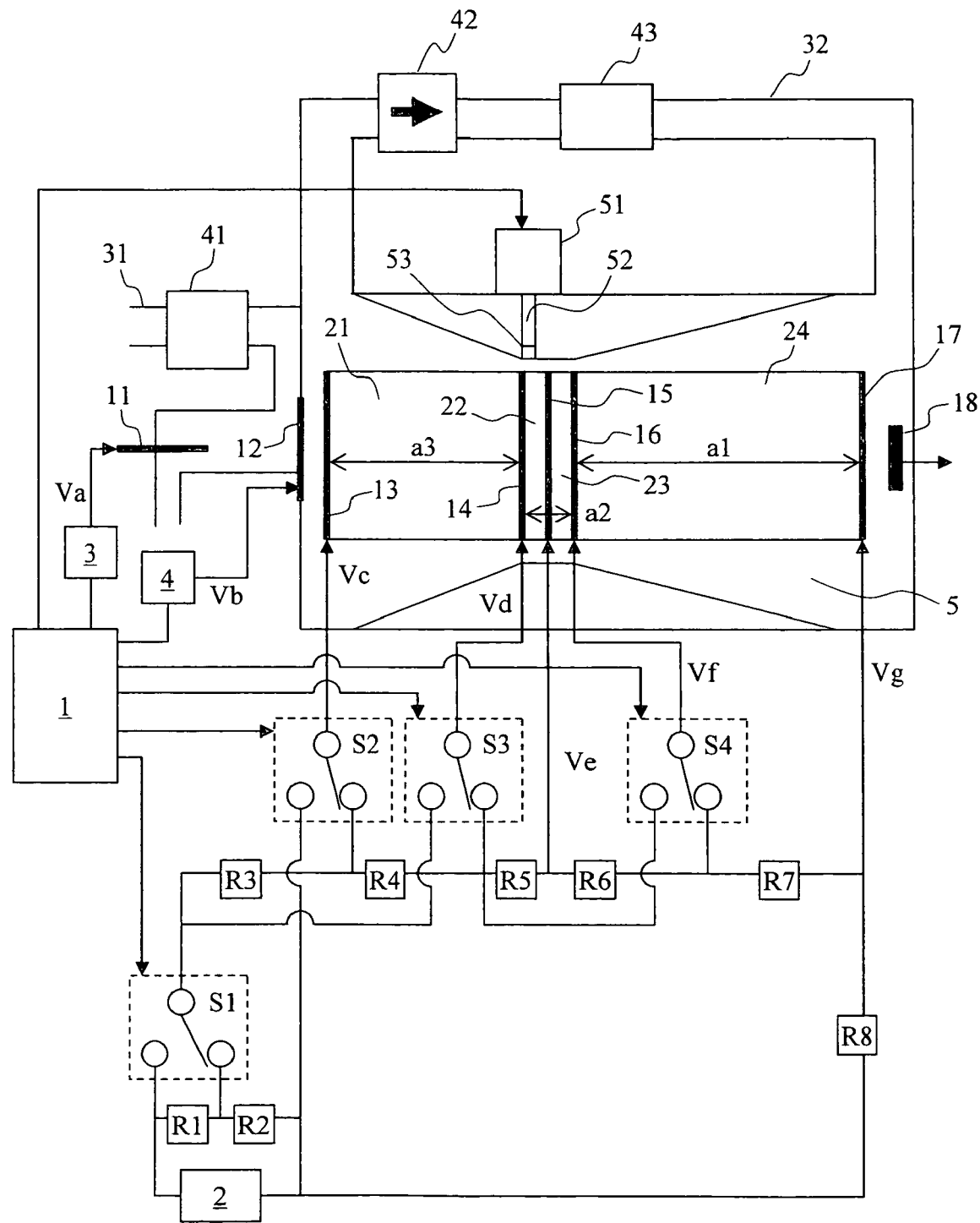
FIG. 1 is a view illustrating a configuration example of an ion mobility spectrometer of the present invention.

FIG. 1 illustrates a configuration example of an ion mobility spectrometer of the present invention. The present apparatus includes a sample gas suction section that sucks sample gas such as air, a corona discharge section for ionizing components in the sample gas, a drift tube 5, a gas flow generation section, a detector 18, a light source 51, and a controller 1. The drift tube 5 is illustrated by a sectional view schematically showing an internal structure.

Figure 2:
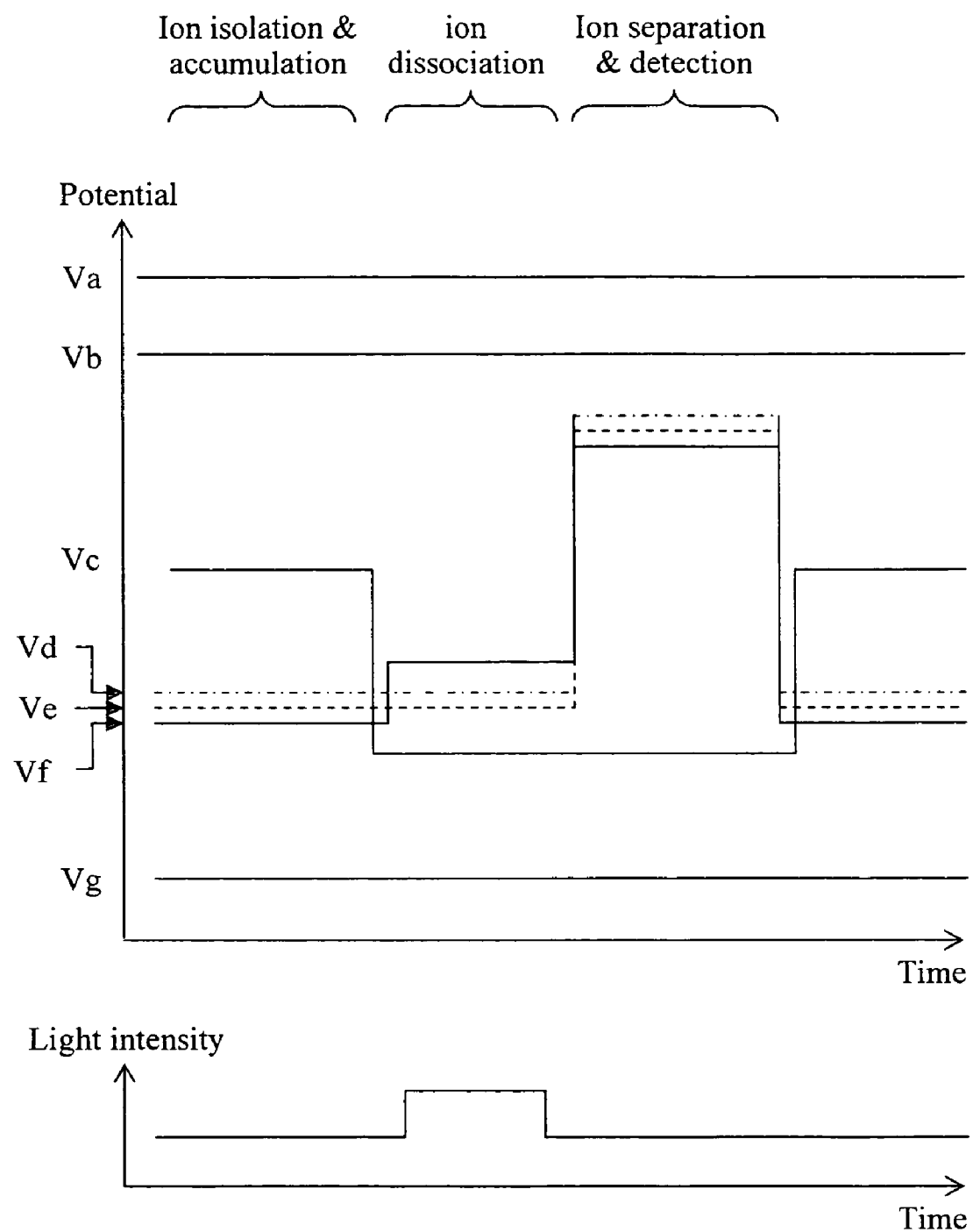
FIG. 2 is a sequence view of an electrode potential and light intensity.

The sample gas suction section is composed of a fan 41 and a pipe 31. The corona discharge section is provided in an interior of the pipe 31 and is composed of a discharge needle 11 and a counter electrode 12. When a potential difference is applied between the discharge needle 11 and the counter electrode 12 by power supply sources 3 and 4 to generate discharge, various components in the sample gas are ionized in the corona discharge section and its vicinity mainly by the principle of chemical ionization. The gas flow generation section is composed of a fan 42 and a pipe 32, and generates an gas flow (hereinafter referred to as a counter flow) which is directed from the detector 18 side to the counter electrode 12 side in the interior of the drift tube 5. The drift tube 5 has a first region a1, a second region a2, and a third region a3. In the first region a1, a flow channel cross-sectional area is gradually decreased in a flow direction of the counter flow. In the second region a2, the flow channel cross-sectional area is substantially constant in the flow direction of the counter flow. In the third region a3, the flow channel cross-sectional area is gradually increased in a flow direction of the counter flow. In an interior of the drift tube 5, electrodes 13 to 17 and resistors 21 to 24 are arranged in a laminated form, and voltage is applied to the electrodes 13 to 17 to thereby form an electric field in the flow direction of the counter flow. The control section 1 has a function of controlling power supply sources 2 to 4 and switches S1, S2, S3 and S4 to switch voltage applied to the electrode of each section. The control section 1 also has a function of controlling a light source 51 to irradiate the second region a2 with light. By controlling voltages (Va to Vf) applied to the electrodes of the respective sections according to a predetermined sequence as illustrated in FIG. 2 and light intensity emitted to the second region a2 from the light source 51, an ion having predetermined ion mobility is isolated and accumulated in the second region a2. Thereafter, the accumulated ion is dissociated to generate fragment ions, and generated fragment ions are separated and detected in decreasing order of ion mobility.

Figure 3:
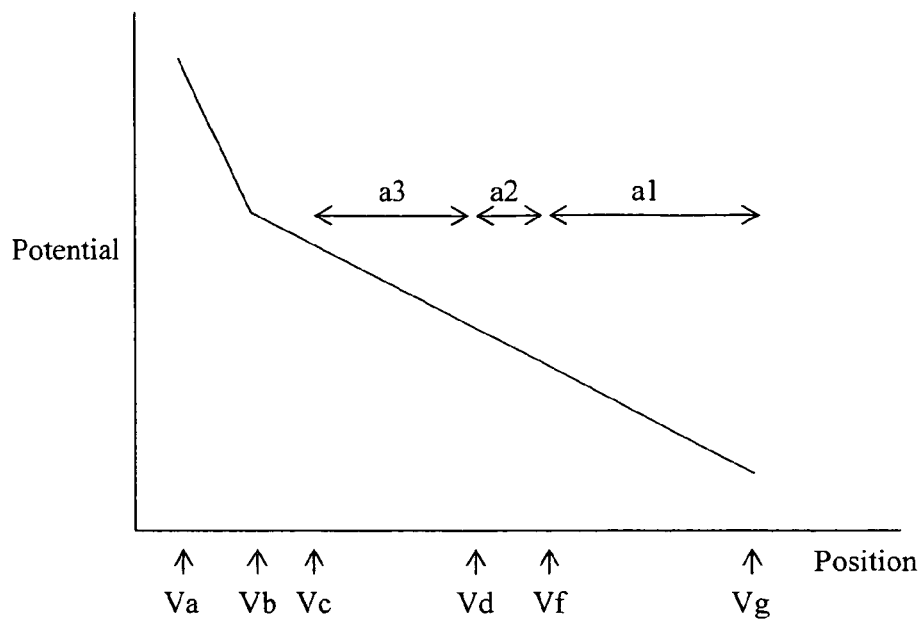
FIG. 3 is a view illustrating a potential distribution in an interior of a drift tube along a flow direction at time of precursor ion isolation and accumulation.
Figure 4:
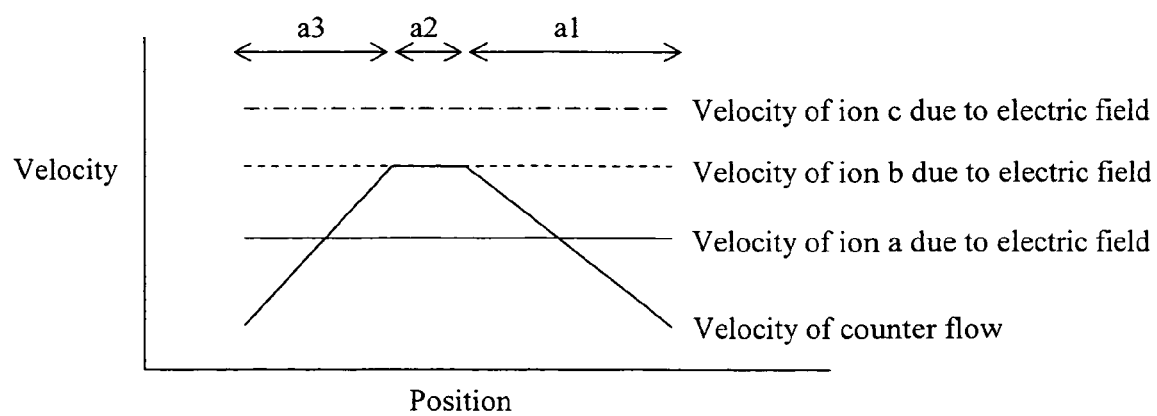
FIG. 4 is a view illustrating a relationship between a flow rate of a counter flow and an ion velocity due to an electric field at the time of precursor ion isolation and accumulation.

FIG. 3 illustrates a potential distribution in the interior of the drift tube along the flow direction in ion isolation and accumulation processes illustrated in FIG. 2. In this potential distribution, the respective potentials of the discharge needle 11, the counter electrode 12, the electrodes 13, 14, 15, 16 and 17, namely, Va, Vb, Vc, Vd, Ve, Vf and Vg decrease in this order. Part of ions generated in the vicinity of the corona discharge section moves to the counter electrode 12 due to the potential gradient and enters the drift tube 5 through an aperture (not illustrated) formed on the counter electrode 12. The ions entering the interior of the drift tube tends to further move to the detector side, but receives resistance force due to the counter flow. Ion velocity due to an electric field is equal to a product of the ion mobility and the electric field. The ion mobility depends on the mass, electric charge and shape of the ions. On the other hand, when there is no electric field, the ions move in the same direction and speed as the counter flow regardless of the mass, electric charge and shape of the ions. FIG. 4 illustrates a relationship between a flow rate of the counter flow along the flow direction in the drift tube and ion velocity due to the electric field, when the potential gradient of a predetermined region including the first region a1, the second region a2 and the third region a3 is substantially constant (case in FIG. 3). An ion b stays in the second region a2 since the flow rate of the counter flow and the ion velocity due to the electric field are coincident with each other in the second region a2. An ion c, having higher ion mobility than that of the ion b, passes through the third region a3 and the second region a2 against resistance of the counter flow and enters the first region a1. In the first region a1, the resistance force due to the counter flow gradually decreases toward the ion travelling direction, and therefore the ion entering the first region a1 reaches the detector 18 speedily and disappears. Accordingly, ions do not stay in the first region a1.

On the other hand, an ion a, having lower ion mobility than that of the ion b, cannot pass through the third region a3 due to the resistance of the counter flow. The ion mobility of the ion staying in the second region a2 depends on the electric field and the flow rate of the counter flow. Therefore, the electric field or the flow rate may be changed to thereby capture an ion having desired ion mobility in the second region a2.

The second region a2 is irradiated with light from the light source 51 to thereby dissociate the ion captured in the second region a2. Light generated by the light source 51 is incident on the second region through an optical path 52 and a lens 53. In general, ion mobility of fragment ions generated is higher than that of the original ion, that is, precursor ion. Accordingly, generated fragment ions leak one after another from the second region a2 and reaches the detector 18 through the first region a1. As a result, resolution of an ion mobility spectrum is reduced.

A reduction in light irradiation time is one of solutions of this problem. A peak width of the ion mobility spectrum is generally several milliseconds, and therefore light irradiation time may be suppressed to about one millisecond in order to obtain sufficient spectrum resolution. However, light irradiation time and generated quantity of ions have a trade-off relationship, and when ion dissociation efficiency is low, there is a case in which desired sensitivity cannot be obtained.

Figure 5:
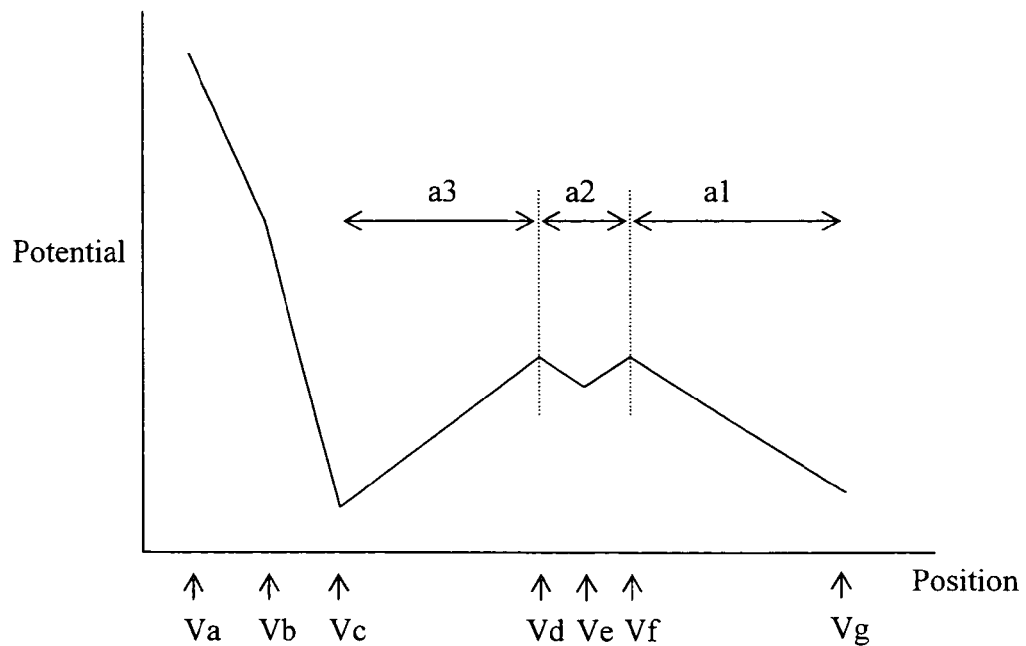
FIG. 5 is a view illustrating a potential distribution in the interior of the drift tube along the flow direction at time of precursor ion dissociation.

FIG. 5 illustrates a potential distribution in the interior of the drift tube along the flow direction in an ion dissociation process illustrated in FIG. 2. In this potential distribution, the potentials Vd, Ve and Vf of the electrodes 14, 15 and 16, respectively, in the second region a2 have a relationship of Vd>Ve<Vf. Accordingly, a potential well, having a bottom placed in the vicinity of the electrode 15, is formed in the second region a2. As a result of forming such a potential well, the fragment ions generated by the light irradiation stay in the vicinity of the electrode 15 of the second region a2. At this time, the potential of the electrode 13 is set to be further lower than that of the electrode 14, that is, Vc<Vd as shown in FIG. 5. By this means, the ion staying in the third region a3 moves to the ion source side and is carried and discharged to the pipe 32 by the flow of the counter flow. A filter 43 is inserted in the middle of the pipe 32 to remove impurities mixed in the counter flow, such as discharged ion or the like.

The light irradiation is limited to a part of an area close to the ion source, the area being formed between the electrodes 14 and 15. In general, the ion mobility of the fragment ions generated by the light irradiation is higher than that of the precursor ions. Accordingly, the fragment ions move toward the vicinity of the electrode 15 at the moment when they are generated. For this reason, it is possible to reduce probability of multistage dissociation where the fragment ions are further dissociated. As a result, this configuration has an effect of preventing a reduction in sensitivity due to multistage dissociation. In addition, movement of the precursor ions stops at the moment when the precursor ions enter the second region a2, and therefore the precursor ions stay, in a concentrated manner, in the part of the second region 2a which is close to the ion source. Therefore, even if the light irradiation is limited to the part of the second region a2 which is close to the ion source, almost all the precursor ions can be irradiated with light.

Using infrared light as irradiation light makes it possible to excite ion oscillation energy to dissociate ions. In this case, fragment ions which are stable in terms of energy are easily generated, and therefore relatively few types of fragment ions, are generated. Hence, signal intensity of each fragment ion is high and its detection is easy. Ultraviolet energy is equal to chemical bond energy in an interior of ions. Accordingly, chemical bond can be directly broken to generate fragment ions. Ions which are not easily dissociated with infrared ray may be dissociated by using ultraviolet ray. A means for dissociating ions is not limited to light irradiation, and means such as particle irradiation of electron, ion, etc., or heating may be used.

Figure 6:
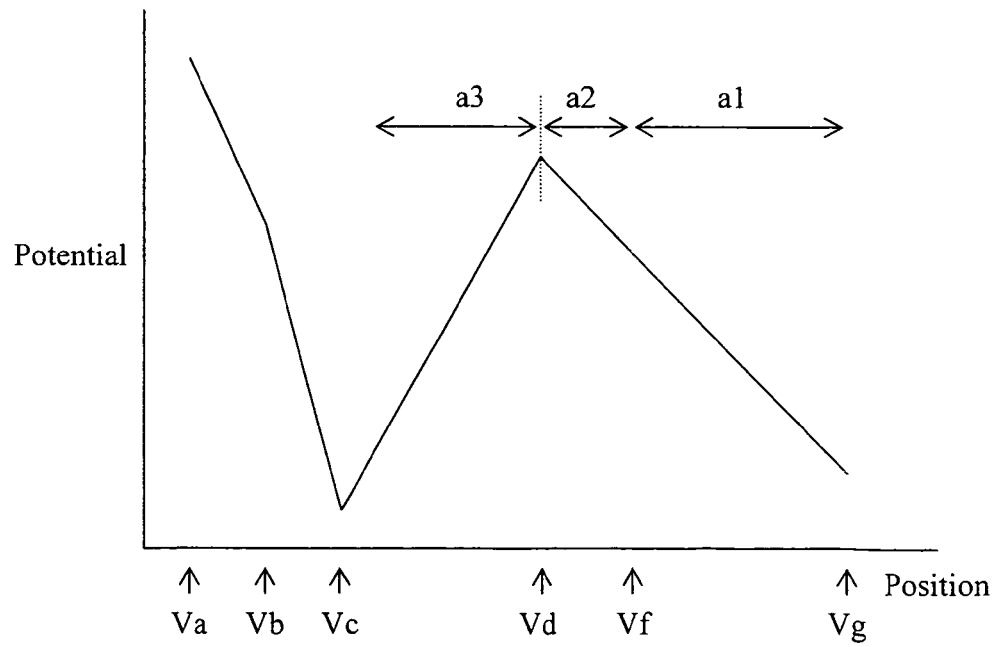
FIG. 6 is a view illustrating a potential distribution in the interior of the drift tube along the flow direction at time of fragment ion separation and detection.

FIG. 6 illustrates a potential distribution in the interior of the drift tube along the flow direction in ion separation and detection processes illustrated in FIG. 2. In this potential distribution, the respective potentials of the electrodes 14, 15, 16 and 17, namely, Vd, Ve, Vf and Vg decrease in this order. Moreover, as illustrated in FIG. 2, potential Vd, Ve and Vf at this time are set to be higher than those in the ion isolation and accumulation processes. By this means, the fragment ions staying in the vicinity of the electrode 15 of the second region a2 and the precursor ions remaining without being dissociated start to move to the detector 18 all at the same time, and reach the detector 18 and are detected in decreasing order of ion mobility. During this time, the potential Vc of the electrode 13 is maintained to be lower than the potential Vd of the electrode 14 as illustrated in FIG. 6. Accordingly, the ions remaining in the third region a3 move to the ion source side and are carried by the flow of the counter flow, and discharged to the pipe 32.

Figure 7:
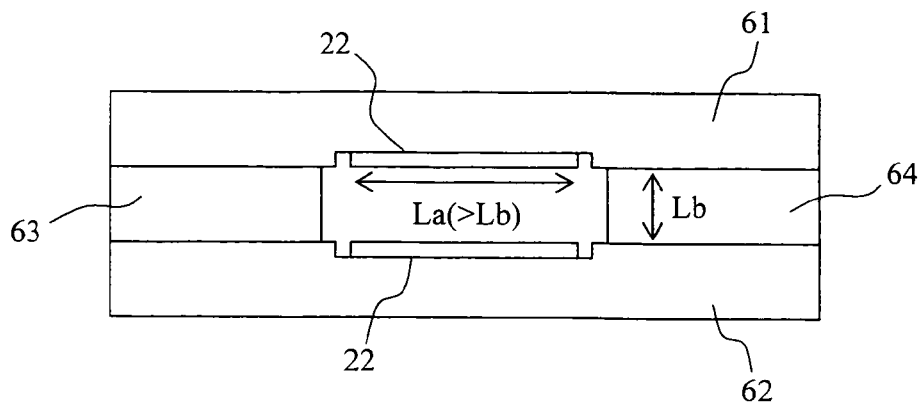
FIG. 7 is a cross-sectional view of the drift tube perpendicular to the flow direction.

FIG. 7 illustrates a conceptual view of an ion mobility spectrum obtained by the present apparatus. The ion mobility spectrum is plotted with a horizontal axis, representing elapsed time after which the potential of each electrode is changed from the potential illustrated in FIG. 5 to the potential illustrated in FIG. 6, and a vertical axis representing an output signal of the detector. The ion b accumulated in the second region a2 in the ion isolation and accumulation processes illustrated in FIG. 2 and fragment ions b-1 and b-2 generated by dissociating the ion b as the precursor ion are observed.

Figure 10:
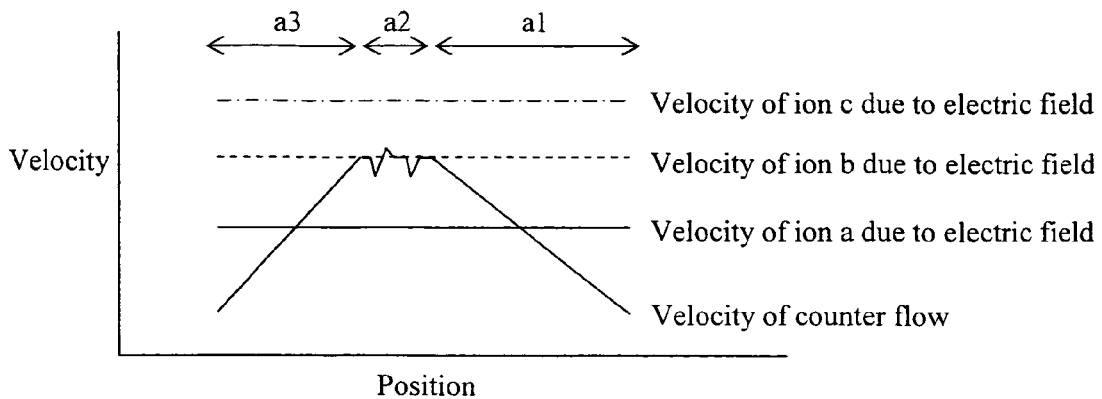
FIG. 10 is a view illustrating a potential distribution of a interior of a drift tube along a flow direction at time of precursor ion isolation and accumulation, when a flow rate in a second region a2 minutely increase and decrease in the flow direction.
Figure 11:
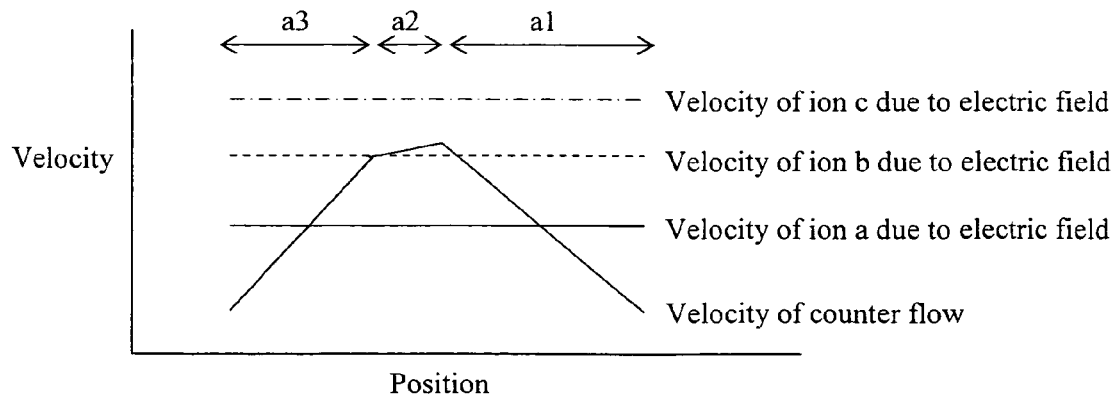
FIG. 11 is a view illustrating a potential distribution of a interior of a drift tube in the flow direction at time of precursor ion isolation and accumulation, when a flow rate in a second region a2 slightly and gradually decrease in the flow direction of a counter flow.

The range of the ion mobility of the ion captured in the second region a2 becomes narrow as the flow rate of the counter flow flowing in the second region becomes uniform, and as a result, resolution of the ion isolation is increased. When the flow rate in the second region a2 minutely increases or decreases in the flow direction as illustrated in FIG. 10 due to minute increase or decrease in the flow channel cross-sectional area of the second area a2, the range of the ion mobility of the ion captured in the second region a2 expands. As a result, the resolution of the ion isolation is lost. Or, when the flow rate in the second region a2 slightly and gradually decreases in the flow direction as illustrated in FIG. 11 due to gradual increase in the flow channel cross-sectional area of the second area a2, the range of the ion mobility of the ion captured in the second region a2 also expands. As a result the resolution of the ion isolation is lost. However, in both cases, a function as an ion isolation section is provided. Namely, the flow channel cross-sectional area of the second area a2 or the flow rate may be maintained substantially constant in the flow direction.

In the general ion mobility spectrometer, a ring electrode and an insulation spacer are laminated in the interior of the drift tube to form an electric field. However, when a structure is provided in the interior of the drift tube, the counter flow is disturbed, and therefore such a structure cannot be adapted in the present apparatus.

Figure 8:
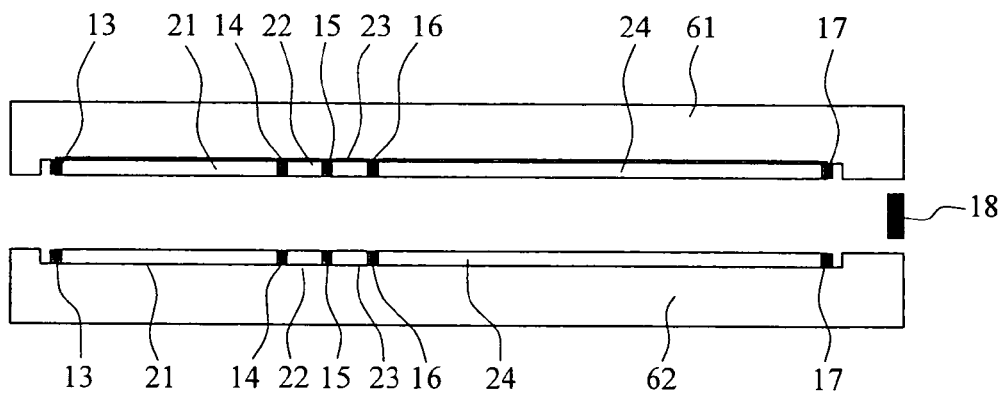
FIG. 8 is a cross-sectional view of a drift tube along the flow direction.
Figure 9:
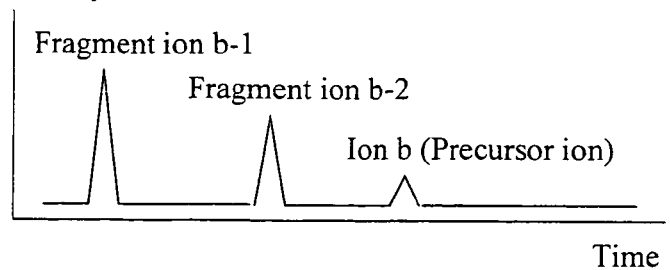
FIG. 9 is a conceptual view of an ion mobility spectrum.

FIG. 8 is a cross-sectional view of the drift tube of the present apparatus which is perpendicular to the flow direction in the second region a2. The internal space of the drift tube 5 is composed of two flat plates 61, 62 and two side plates 63 and 64 which are bonded to one another and a cross-sectional shape perpendicular to the flow direction is rectangular. Each of the flat plates 61 and 62 has a groove on its surface that forms an inner wall of the drift tube and a plate-like resistor 22 is buried in each groove. The shape of the resistor substantially coincides with that of the groove, and has a fixed width La and a fixed thickness. The resistor is made of, for example, glass, and a resistance value of each resistor ranges from about one megaohm to one gigaohm. FIG. 9 is a cross-sectional view of the drift tube along the flow direction. Thin plate-like electrodes 13 to 17 are arranged in close contact with the end surfaces of the resistors 21 to 24. The size of each of the electrodes 13 to 17 substantially coincides with that of the end surface of the resistors, and does not protrude from the end surface of resistors. The aforementioned structure makes it difficult to generate turbulence of the counter flow. As a result, it is possible to suppress deterioration in a capture efficiency of the precursor ion and the isolation resolution thereof, and the separation resolution of the fragment ion.

There can be considered a structure such that the cross-sectional shape of the drift tube is circular and the cross-sectional area is increased and decreased in the flow direction. However, if resistors to be arranged on the inner wall surface of the drift tube having such a shape are manufactured, a manufacturing cost will be high and result in a high apparatus cost. With the structure in which the cross section perpendicular to the flow direction is rectangular as illustrated in FIG. 8, the flat plate-like resistors can be used. This makes it possible to provide not only a low-priced apparatus but also an advantage where the apparatus can be miniaturized.

Neither resistors nor electrodes are arranged on the side plates 63 and 64, and therefore there exist electric field components moving from each of the resistors or electrodes to the side plates 63 and 64. When the influence of the electric field components is large, the ions move from the vicinity of the axis of the drift tube 5 to the side plates 63 and 64. As a result, there is a possibility that the amount of ions reaching the detector will be decreased to reduce detection sensitivity. For this reason, as illustrated in FIG. 8, the width La of the plate-like resistor is set to be larger than the interval Lb between opposing plate-like resistors. Preferably La is set to be twice as large as Lb. By this means, the velocity of the ions, which move from the vicinity of the axis of the drift tube 5 to the side plates 63 and 64, is decreased. As a result, the reduction in detection sensitivity is suppressed.

The ion mobility spectrometer of the present invention can be used as a detector for harmful substances in the air. Particularly, the present invention is used as a portable detector.

EXPLANATION OF REFERENCE NUMERALS

1 . . . control section, 2 to 4 . . . power supply sources, 5 . . . drift tube, 11 . . . discharge needle, 12 . . . counter electrode, 13 to 17 . . . electrodes, 18 . . . detector, 21 to 24 . . . resistors, 31, 32 . . . pipes, 41, 42 . . . fans, 43 . . . filter, 51 . . . light source, 52 . . . optical path, 53 . . . window, 61, 62 . . . flat plates, 63, 64 . . . side plates, a1 . . . first region, a2 . . . second region, a3 . . . third region, Va, Vb, Vc, Vd, Ve, Vf . . . potentials, S1, S2, S3, S4 . . . switches, and R1, R2, R3, R4, R5, R6, R7, R8 . . . electric resistances

What is claimed is:

1. An ion mobility spectrometer comprising:
a flow channel having a first region where a flow rate gradually increases in a flow direction, a second region where the flow rate is substantially constant, and a third region where the flow rate gradually decreases, the first to third regions arranged in this order from an upstream side of flow to a downstream side thereof;
an electric field forming mechanism that forms an electric field in an interior of the flow channel in the flow direction;
an ion generating section placed on a downstream side of the third region;
an ion detector placed on an upstream side of the first region; and
an energy supply mechanism that supplies energy to the second region.

2. The ion mobility spectrometer according to claim 1, further comprising a control mechanism that controls the electric field forming mechanism and the energy supply mechanism so that ions having predetermined ion mobility are accumulated in the second region, and that fragment ions are generated by supplying energy to the second region to dissociate the ion having the predetermined ion mobility, and that the fragment ions are then detected in decreasing order of ion mobility.

3. The ion mobility spectrometer according to claim 2, wherein the electric field forming mechanism can independently set the electric field intensity of each of the first region, the second region and the third region.

4. The ion mobility spectrometer according to claim 2, wherein the electric field forming mechanism can independently set the electric field intensity of each of a partial region of the second region in an upstream side of flow and a partial region of the second region in a downstream side.

5. The ion mobility spectrometer according to claim 3, wherein the control mechanism controls the electric field forming mechanism to reverse a direction of a first electric field and a direction of a second electric field, the first electric field being formed in the third region in a flow direction during a time period when the energy is supplied to the second region from the energy supply mechanism or when the fragment ions are detected by the ion detector, and the second electric field being formed in the third region in the flow direction during a time period when an ion having a predetermined ion mobility is accumulated in the second region.

6. The ion mobility spectrometer according to claim 4, wherein the control mechanism controls the electric field forming mechanism to form a potential well, having a bottom placed in the vicinity of a boundary between the partial region of the second region in the upstream side of flow and the partial region of the second region in the downstream side, during a time period when the energy is supplied to the second region from the energy supply mechanism.

7. The ion mobility spectrometer according to claim 1, wherein
a flow channel cross section in the second region is substantially rectangular, and
the electric field forming mechanism has a resistor buried in a flow channel inner wall extending in a longitudinal direction of the flow channel cross section.

8. The ion mobility spectrometer according to claim 4, wherein
a flow channel cross section in the second region is substantially rectangular,
the electric field forming mechanism has, in flow channel inner walls extending in a longitudinal direction of the flow channel cross section and facing each other: a pair of first electrodes formed facing each other at a downstream side part of the third region; a pair of second electrodes formed facing each other at a boundary part between the third region and the second region; a pair of third electrodes formed facing each other at a boundary part between the partial region of the second region in the upstream side and the partial region of the second region in the downstream side; a pair of fourth electrodes formed facing each other at a boundary part between the second region and the first region; and a pair of fifth electrodes formed facing each other at an upstream side part of the first region, and
the electric field forming mechanism also has, in the flow channel inner walls extending in a longitudinal direction of the flow channel cross section and facing each other, resistors buried between the first electrodes and the second electrodes, between the second electrode and the third electrodes, between the third electrode and the fourth electrode, and between the fourth electrode and the fifth electrode.

* * * * *